(12) United States Patent
Wehner et al.

(10) Patent No.: US 6,232,375 B1
(45) Date of Patent: May 15, 2001

(54) 4-AMINOPYRIMIDINONES AND OXAZOLIDINO-4-AMINOPYRIMIDINONES, PROCESS FOR THEIR PREPARATION AND THEIR USE FOR STABILIZING HALOGEN-CONTAINING POLYMERS

(75) Inventors: Wolfgang Wehner, Zwingenberg; Hans-Helmut Friedrich, Lautertal, both of (DE)

(73) Assignee: Witco Vinyl Additives GmbH, Lampertheim (DE)

( * ) Notice: Subject to any disclaimer, the term of this patent is extended or adjusted under 35 U.S.C. 154(b) by 0 days.

(21) Appl. No.: 09/542,327

(22) Filed: Apr. 4, 2000

(30) Foreign Application Priority Data

Apr. 6, 1999 (DE) ................................. 199 15 388

(51) Int. Cl.[7] ............................... C08K 5/34; C08K 5/15; C08K 5/05
(52) U.S. Cl. ........................... 524/98; 524/100; 524/114; 524/379; 524/400; 524/427; 524/430; 524/493; 544/235
(58) Field of Search ............................. 524/98, 100, 114, 524/379, 400, 427, 430, 493; 544/235

(56) References Cited

U.S. PATENT DOCUMENTS

| 3,436,362 | 4/1969 | Hayer et al. . |
| 4,000,100 | 12/1976 | Baldyga . |
| 4,590,233 | 5/1986 | Erwied et al. . |
| 4,656,209 | 4/1987 | Wehner et al. . |
| 4,963,608 | 10/1990 | Kunieda et al. . |
| 5,004,776 | 4/1991 | Tadenuma et al. . |
| 5,034,443 | 7/1991 | Bae et al. . |
| 5,216,058 | 6/1993 | Visneski . |
| 5,859,100 | 1/1999 | Wehner et al. . |

FOREIGN PATENT DOCUMENTS

| 2187708 | 4/1997 | (CA) . |
| 40 31 818 A1 | 4/1992 | (DE) . |
| 10-110024 | 4/1998 | (JP) . |
| WO 99/48941 | 9/1999 | (WO) . |

*Primary Examiner*—Kriellion Sanders
(74) *Attorney, Agent, or Firm*—Scully, Scott, Murphy & Presser

(57) ABSTRACT

The invention relates to 4-aminopyrimidinediones and oxazolidino-4-aminopyrimidinediones of the formula I and II given below, a process for their preparation, their use for stabilizing halogen-containing polymers, and compositions composed of compounds of the formula I or II and of chlorine-containing polymers, in particular PVC.

20 Claims, No Drawings

4-AMINOPYRIMIDINONES AND OXAZOLIDINO-4-AMINOPYRIMIDINONES, PROCESS FOR THEIR PREPARATION AND THEIR USE FOR STABILIZING HALOGEN-CONTAINING POLYMERS

The invention relates to 4-aminopyrimidinones and oxazolidino-4-aminopryimidinones of the formulae I and II given below, a process for their preparation, their use for stabilizing halogen-containing polymers, and compositions composed of compounds of the formula I and II and of chlorine-containing polymers, in particular PVC.

BACKGROUND OF THE INVENTION

There is a wide variety of additives for of stabilizing PVC. Particularly suitable for this purpose are compounds of lead, of barium and of cadmium, but nowadays these are contentious for environmental reasons or due to their heavy metal content (cf.,pages 303–311, and "Kunststoff Handbuch PVC" ["Plastics Handbook PVC"], Vol. 2/1, W. Becker/ D.Braun, Carl Hanser Verlag, $2^{nd}$ Ed., 1985, pages 531–538; and also Kirk-Othmer: "Encyclopedia of Chemical Technology", $4^{th}$ Ed., 1994, Vol. 12, Heat Stabilizers, pp. 1071–1091). Further attempts are therefore being made to find effective stabilizers or stabilizer combinations which are free from lead, barium and cadmium.

1,3-disubstituted aminopyrimidinediones have already been described in U.S. Pat. No. 3,436,362, U.S. Pat. No. 4,656,209, U.S. Pat. No. 4,352,903 and EP-A-0 768 336, and can be prepared by known methods in one (or more) steps.

It has now been found that 1,3-disubstituted 4-aminopyrimidinediones and oxazolidino-4-aminopyrimidinediones of the general formulae I and II and particularly suitable for stabilizing chlorine-containing polymers, in particular PVC.

SUMMARY OF THE INVENTION

The present invention therefore provides compounds of the general formulae I and II

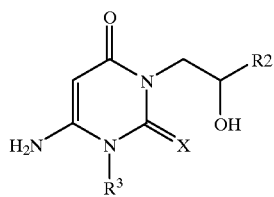

(I)

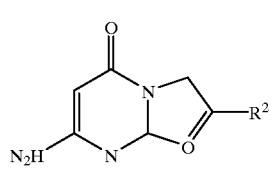

(II)

where X=O or S, preferably O, $R^2$=H, or the radicals $C_1$–$C_{14}$-alkyl, $C_2$–$C_4$-alkenyl, unsubstituted or substituted $C_4$–$C_8$-cycloalkyl, $C_6$–$C_{10}$-aryl, $C_7$–$C_{10}$-alkaryl, $C_7$–$C_{10}$-aralkyl, —$CH_2$—X—$R^4$, with $R^4$=H, $C_1$–$C_{10}$-alkyl, $C_2$–$C_4$-alkenyl or $C_4$–$C_8$-cycloalkyl, if desired containing an oxirane ring or, if desired, substituted 1–3 times with $C_1$–$C_4$-alkyl, and unsubstituted or substituted benzoyl or $C_2$–$C_{18}$-acyl radical, and preferably $R^2$=H, methyl, ethyl, allyl, phenyl, —$CH_2$—X—$R^4$, with $R^4$=H, an n-propyl, isopropyl, 2-ethylhexyl, n-butyl, isobutyl, sec-butyl, tert-butyl, allyl, methallyl, phenyl, cresyl radical; in particular $R^2$=ethyl, —$CH_2$—X—$R^4$, where $R^4$=H, n-propyl, isopropyl, allyl, $R^3$=$R^2$, $R^4$ or $C_2$–$C_6$-alkyl substituted with at least 1 to 5 OH groups and/or interrupted by at least 1 to not more than 4 oxygen atoms, or $C_3$–$C_8$-alkenyl or —$CH_2$—$CH(OH)R^2$, preferably $R^3$=a methyl, phenyl, benzyl radical, in particular the methyl radical.

DETAILED DESCRIPTION OF THE INVENTION 1. aminouracils of the type

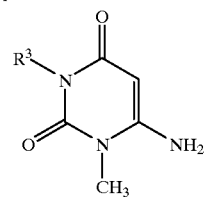

2. aminouracils of the type

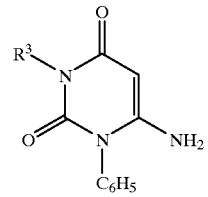

3. aminouracils of the type

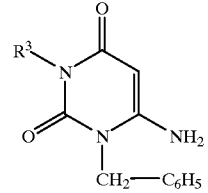

4. aminouracils of the type

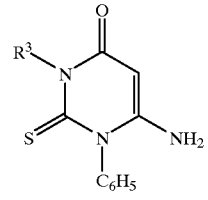

5. aminouracils of the type

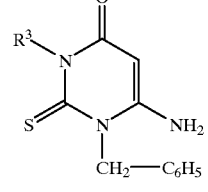

with $R^3$=—$CH_2CH_2OH$, —$CH_2$—$CHOH$—$CH_3$, —$CH_2$—$CHOH$—$C_2H_5$, —$CH_2$—$CHOH$—$^nC_3H_7$, —$CH_2$—$CHOH$—$^nC_4H_9$;

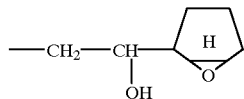

—CH$_2$—CHOH—CH$_2$—O—$^n$C$_3$H$_7$, —CH$_2$—CHOH—CH$_2$—O—$^i$C$_3$H$_7$,

—CH$_2$—CHOH—CH$_2$—O—$^n$C$_4$H$_9$, —CH$_2$—CHOH—CH$_2$—O—$^i$C$_4$H$_9$,

—CH2—CHOH—CH$_2$—O—$^{sec}$C$_4$H$_9$, —CH$_2$—CHOH—CH$_2$—O—$^t$C$_4$H$_9$,

—CH$_2$—CHOH—CH$_2$—O—2-ethylhexyl, -allyl, -phenyl, -o-cresyl, -m-cresyl, -p-cresyl; -pentanoyl, -neohexanoyl, -neoheptanoyl, -neooctanoyl, -neononanoyl, -neodecanoyl.

According to the invention, particular preference is given to the compounds with $R^2$=alkyl=pentyl, hexyl, heptyl, octyl, nonyl, decal, undecyl, dodecyl, tridecyl, and tetradecyl, preferably hydrogen, methyl, ethyl, n-propyl, isopropyl, n-butyl, isobutyl, sec-butyl, or tert-butyl, and particularly preferably methyl and ethyl;

$R^2$=C$_6$–C$_{10}$-aryl or C$_7$–C$_{10}$-alkaryl=tolyl, xylyl, mesityl, propylphenyl, butylphenyl, trimethoxyphenyl, diethoxyphenyl, propoxyphenyl, or butoxyphenyl, preferably phenyl.

R$_2$=C$_7$–C$_{10}$-aralkyl=benzyl, α- or β-phenylethyl, phenylpropyl or phenylbutyl.

Preference is given to benzyl and β-phenylethyl, particularly preferably benzyl.

R$_2$=C$_4$–C$_8$-cycloalkyl cyclopentyl and cyclohexyl, methylcyclohexyl or trimethylcyclohexyl, preferably cyclohexyl.

R$_4$=H, C$_1$–C$_{10}$-alkyl, C$_2$–C$_4$-alkenyl, phenyl or benzyl, preferably ethyl, propyl, butyl, allyl, methallyl. Particular preference is given to propyl, butyl, allyl.

R$_4$=C$_2$–C$_{18}$-acyl=acetyl, propionyl, butyryl, caproyl, decanoyl, lauryl, myristoyl, palmitoyl or stearoyl. Unsubstituted or substituted benzoyl is trimethylbenzoyl or trimethoxybenzoyl; preference is given to acetyl, propionyl, decanoyl and benzoyl and neodecanoyl is particularly preferred.

R$_4$=cycloaklyl=cyclohexylmethyl, cyclohexylethyl, cyclohexylpropyl or cyclohexylbutyl R$^4$=butenyl, hexenyl, heptenyl or octenyl; preferably allyl or methallyl.

Other preferred compounds of the formula I or II are those with X=O or of the formula I with X=S, and particular preference is given to compounds of the formula I with X=O.

The invention also provides a process for preparing the compounds of the general formulae I and II.

The invention also provides the use of the compounds of the general formulae I and II for stabilizing chlorine-containing polymers, in particular polyvinyl chloride (PVC) and recycled materials from these.

The invention therefore also provides compositions made from at least one of the compounds of the general formula I and/or at least one of the compounds of the general formula II and from chlorine-containing polymers, in particular PVC, and recycles materials from these.

The remaining subject matter of the invention is given in the claims.

The novel compounds of the formula I may be prepared from compounds of the general formula III or IV

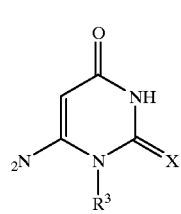
(III)

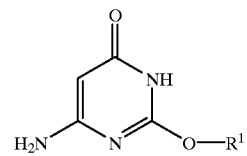
(IV)

where $R^1$ is a branched or unbranched C$_1$–C$_4$-alkyl radical, in particular the methyl or ethyl radical, with an epoxy compound of the general formula V

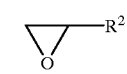

where $R^2$ is as defined above, in a solvent, if desired at elevated pressure, and with a catalytic amount of base.

The compounds of the formulae III and IV are prepared by known methods (e.g. V. Papesch and E. F. Schroeder, J. Org. Chem., 1951 (16), 1879–1890; A. H. Nathan and M. T. Bogert, JACS 63, 2567 (1941); W. Pfleiderer, Chem. Ber., 90, 2272 (1957) or DRP 155 732 (1903) Farbenfabriken Bayer).

The compounds of the general formula (V) are aliphatic, cycloaliphatic, aromatic, araliphatic or alkaromatic epoxy compounds, where $R^2$ is as defined above, for example ethylene oxide, propylene oxide, butylene oxide,

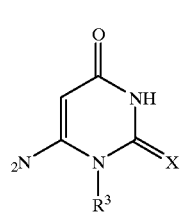
(III)

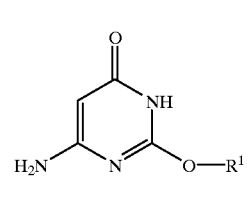
(IV)

hexylene oxide, styrene oxide, glycidol, glycidyl ethers or glycidyl thioethers, such as ethyl, propyl, butyl, hexyl, octyl, allyl, or phenyl ethers, or glycidyl esters based on aliphatic and/or aliphatic aromatic alcohols, in particular unbranched or branched aliphatic monofunctional alcohols, such as methanol, ethanol, n-propanol, isopropanol, butanol, sec-butanol, 2-methyl-1-propanol, 2-methyl-2-propanol, 2-ethylhexanol; or aromatic alcohols, such as phenol, cresol, p-tert-butylphenol, thymol, benzyl alcohol.

These are commercially available products which are sold by their chemical designation or by the respective trade name, such as EUREPOX® RV-K, EUREPOX® RV-P, EUREPOXS RV-A (EUREPOX®=trademark of Witco GmbH) or Grilonit® V 51–54, Grilonit® RV 1802, Grilonit® 1804, Grilonit® 1805, Grilonit® 1807 (Grilonit®=trademark of EMS–Chemie) or Araldit® DY 0390, Araldit® DY 0391 (Araldit®=trademark of CIBA Spezialitäten Chemie).

According to the invention, the process for preparing the novel compounds of the general formulae I and II is preferably carried out by reacting a mixture of one mole of a compound of the general formula III or IV, 200–500 ml of a solvent, 0.01–0.3 mol of a base and 1–2, preferably 1–1.5 mol of a compound of the general formula V for 1–10 h at 20–150° C., preferably 40–90° C., if desired under elevated pressure.

The solvents used preferably comprise polar, protic and/or aphotic solvents, such as water, methanol, ethanol, propanol or other water-miscible solvents, such as acetone, tetrahydrofuran (THF), dioxane, dimethylformamide (DMF), dimethylacetamide (DMA) or mixtures of these. These selection depends on the nature of the radicals $R^1$, $R^2$, $R^3$ in the general formulae III, IV and V. The starting materials should be partially or completely soluble in these. If desired, concomitant use may be made of the common phase-transfer catalysts, e.g. quaternary ammonium salts, such as tetrabutylammonium bromide.

The bases used comprise alkali metal/alkaline earth metal hydroxides, in particular NaOH and KOH, alkali metal alcoholates, alkali metal salts of an organic/inorganic acid, for example sodium acetate and tertiary amines, such as triethylamine, tributylamine, pyridine, dimethylaniline and dimethylaminopyridine, and also basic anion-exchangers.

The skilled worker will, as a matter of routine, be able to undertake other modifications and/or optimization of the above process, without the need for any inventive activity.

To achieve stabilization in the chlorine-containing polymer, it is expedient to use from 0.01 to 10 parts by weight, preferably from 0.05 to 5 parts by weight, in particular from 0.1 to 3 parts by weight, of the compounds of the formula I and II, based on 100 parts by weight of PVC.

The invention also provides combinations of compounds of the general formula I and/or of the general formula II with at least one other conventional additive and/or stabilizer. Preference is given to polyols and disaccharide alcohols, perchlorate compounds, glycidyl compounds, hydrotalcite, zeolite (aluminosilicates of alkali metals and/or of alkaline earth metals), fillers, metal soaps, compounds of alkali metals and of alkaline earth metals, lubricants, plasticizers, phosphites, pigments, epoxidized fatty acid esters and other epoxy compounds, antioxidants, UV absorbers and light stabilizers, blowing agents.

Examples of additional components of this type are listed and explained below (cf. "Handbook of PVC-Formulating" by E. J. Wickson, John Wiley & Sons, New York 1993).

Polyols and Disaccharide Alcohols

Examples of possible compounds of this type are: pentaerythritol, dipentaerythritol, tripentaerythritol, trimethylolethane, bistrimethylolpropane, polyvinyl alcohol, bistrimethyolethane, trimethylolpropane, sugars, sugar alcohols. Among these, preference is given to the disaccharide alcohols.

Polyol syrups, such as sorbitol syrup, mannitol syrup and maltitol syrup, may also be used.

The polyols may be used in amounts of, for example, 0.01 to 20 parts by weight, expediently from 0.1 to 20 parts by weight and in particular from 0.1 to 10 parts by weight, based on 100 parts by weight of PVC.

Perchlorate Compounds

Examples are those of the formula $M(ClO_4)_n$, where m is Li, Na, K, Mg, Ca, Sr, Ba, Zn, Al, La or Ce. The index n corresponds to the valency of M 1,2 or 3. The perchlorate salts may have been complexed or dissolved using alcohols (polyols, cyclodextrins) or ether alcohols and/or ester alcohols.

The perchlorate salts may be used in various common usage forms; e.g. as a salt or solution in water or in an organic solvent as such or, respectively, applied to a support material.

Other embodiments are described in EP 0 394 547, EP 0 457 471 and WO 94/24200.

The perchlorates may be used in amounts of, for example, from 0.01 to 5 parts by weight, expediently from 0.01 to 3 parts by weight, particularly preferably 0.01 to 2 parts by weight, based on 100 parts by weight of PVC.

Glycidyl Compounds

These contain the glycidyl group

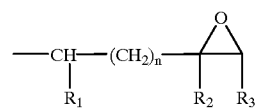

where this has been bonded directly to carbon, oxygen atoms, nitrogen atoms or sulfur atoms, where either $R_1$ and $R_3$ are both hydrogen, $R_2$ is hydrogen or methyl and n=0, or where $R_1$ and $R_3$ together are —$CH_2$—$CH_2$— or —$CH_2$—$CH_2$—$CH_2$—, $R_2$ is then hydrogen and n=0 or 1. It is preferable to use glycidyl compounds having two functional groups. However, it is also possible in principle to use glycidyl compounds with one, three or more functional groups.

Use is predominantly made of diglycidyl compounds having aromatic groups.

The terminal epoxy compounds may be used in amounts of preferably at least 0.1 part, preferably 0.1 to 50 parts by weight, expediently 1 to 30 parts by weight and in particular 1 to 25 parts by weight, based on 100 parts by weight of PVC.

Hydrotalcites

The chemical composition of these compounds is known to the skilled worker, e.g. from the patents DE 3 843 581, U.S. Pat. No. 4,000,100, EP 0 062 813 and WO93/20135.

Compounds from the hydrotalcite series may be described by the following general formula:

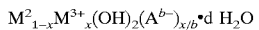

where
$M^{2+}$=one or more of the metals selected from the group consisting of Mg, Ca, Sr, Zn, and Sn.
$M^{3+}$=Al or B,
$A^n$ an anion of valency n,
b is a number from 1–2
$0<x<0.5$,
m is a number from 0–20.
Preference is given to compounds with
$A^n$=$OH^-$, $ClO_4^-$, $HCO_3^-$, $CH_3COO^-$, $C_6H_5COO^-$, $CO_3^{2-}$, $(CHOHCOO)_2^{2-}$, $(CH_2COO)_2^{2-}$, $CH_3CHOHCOO^-$, $HPO_3^-$ or $HPO_4^{2-}$, Examples of hydrotalcites are
$Al_2O_3 \cdot 6MgO \cdot CO_2 \cdot 12H_2O$ (i), $Mg_{4.5}Al_2(OH)_{13} \cdot CO_3 \cdot 3.5H_2O$ (ii), $4MgO \cdot Al_2O_3 \cdot CO_2 \cdot 9H_2O$ (iii), $4MgO \cdot Al_2O_3 \cdot CO_2 \cdot 6H_2O$, $ZnO \cdot 3MgO \cdot Al_2O_{3,co}28$-$9H_2O$ and $ZnO \cdot 3MgO \cdot Al_2O_3 \cdot CO_2 \cdot 5 \text{-} 6H_2O$.

Very particular preference is given to types i, ii and iii.

Zeolites (aluminosilicates of alkali metals and/or of alkaline earth metals)

These may be described by the following general formula: $M_{x/n}[(AlO2)_x(SiO_2)_y] \cdot wH_2O$, where n is the charge from the cation M; M is an element of the first or second main group, such as Li, Na, K, Mg, Ca, Sr, or Ba;

y:x is a number from 0.8 to 15, preferably from 0.8 to 1.2; and w is a number from 0 to 300, preferably from 0.5 to 30. Examples of zeolites are sodium aluminosilicates of the formulae $Na_{12}Al_{12}Si_{12}O_{48} \cdot 27\ H_2O$ [zeolite A], $Na_6Al_6Si_6O_{24} \cdot 2NaX \cdot 7.5\ H_2O$, X=OH, halogen, $ClO_4$ [sodality]; $Na_6Al6Si_{30}O_{72} \cdot 24\ H_2O$; $Na_8Al_8Si_{40}O_{96} \cdot 24\ H_2O$; $Na_{16}Al_{16}Si_{24}O_{80} \cdot 16\ H_2O$; $Na_{16}Al_{16}Si_{32}O_{96} \cdot 16\ H_2O$; $Na_{56}Al_{56}Si_{136}O_{384} \cdot 250\ H_2O$ [zeolite Y], $Na_{86}Al_{86}Si_{106}O_{384} \cdot 264\ H_2O$ [zeolite X]; or the zeolite which can be prepared by partial or complete exchange of the Na atoms by Li atoms, K atoms, Mg atoms, Ca atoms, Sr atoms of Zn atoms, for example.

$(Na,K)_{10}Al_{10}Si_{22}O_{64} \cdot 20\ H_2O$; $Ca_{4.5}Na_3[(AlO_2)_{12}(SiO_2)_{12}] \cdot 30\ H_2O$; $K_9Na_3[(AlO_2)_{12}(SiO_2)_{12}] \cdot 27\ H_2O$. Very particular preference is given to Na zeolite A and Na zeolite P.

The hydrotalcites and/or zeolite may be used in amounts of, for example, 0.1 to 20 parts by weight, expediently 0.1 to 10 parts by weight and in particular 0.1 to 5 parts be weight, based on 100 parts by weight of halogen-containing polymer.

Fillers

Filler such as calcium, carbonate, dolomite, wallastonite, magnesium oxide, magnesium hydroxide; silicates, china clay, talc, glass fibers, glass beads, wood flour, mica, metal oxides or metal hydroxides, carbon black, graphite, rock flour, heavy spar, glass fibers, talc, kaolin and chalk are used. Preference is given to chalk (HANDBOOK OF PVC FORMULATING E. J. Wickson, John Wiley & Sons, Inc. 1993, pp. 393–449) and reinforcing agents (TASCHENBUCH der Kunststoffadditive [Plastics Additives Handbook], R. Gachter & H. Muller, Carl Hanser, 1990, pp. 549–615).

The fillers may be used in amounts of preferably at least one part, for example 5 to 200 parts by weight, expediently 10 to 150 parts by weight and in particular from 15 to 100 parts by weight, based on 100 parts by weight of PVC.

Metal Soaps

Metal soaps are primarily metal carboxylates, preferably of relatively long-chain carboxylic acids. Well known examples of these are stearates and laureates and also oleates and salts of relatively short-chain aliphatic or aromatic carboxylic acids, such as acetic acid, propionic acid, butyric acid, valeric acid, hexanoic acid, sorbic acid, oxalic acid, malonic acid, succinic acid, glutaric acid, adipic acid, fumaric acid, citric acid, benzoic acid, salicylic acid, phthalic acids, hemimellitic acid, trimellitic acid, pyromellitic acid.

Metals which should be mentioned are: Li, Na, K. Mg, Ca, Sr, Ba, Zn, Al, La, Ce and rare earth metals. use is frequently made of so-called synergistic mixtures, such as barium/zinc stabilizers, magnesium/zinc stabilizers, calcium/zinc stabilizers or calcium/magnesium/zinc stabilizers. The metal soaps may be used either along or in mixtures. An overview of common metal soaps is found in Ullmann's Encyclopedia of Industrial Chemistry, $5^{th}$ Ed., Vol. A16 (1985), pp. 361 et seq.

The metal soaps or mixtures of these may be used in amounts of, for example, 0.001 to 10 parts by weight, expediently 0.01 to 8 parts by weight, particularly preferably 0.05 to 5 parts by weight, based on 100 parts by weight of PVC.

Compounds of Alkali Metals and of Alkaline Earth Metals

For the purposes of the present invention, these are mainly the carboxylates of the acids described above, but also corresponding oxides or, respectively, hydroxides or carbonates. Mixtures of these with organic acids are also possible. Examples are LiOH, NaOH, KOH, CaO, $Ca(OH)_2$, MgO, $Mg(OH)_2$, $Sr(OH)_2$, $Al(OH)_3$, $CaCO_3$ and $MgCO_3$ (and also basic carbonates, such as magnesia alba and huntite), and also fatty-acid salts of Na and of K. In the case of alkaline earth carboxylates and Zn carboxylates it is also possible to use adducts of these with MO or $M(OH)_2$ (M=Ca, Mg, Sr or Zn), so-called "overbased" compounds. In addition to the stabilizers according to the invention it is preferable to use alkali metal carboxylates, alkaline earth metal carboxylates and/or aluminum carboxylates.

Lubricants

Examples of possible lubricants are: montan wax, fatty acid esters, PE waxes, amide waxes, chloroparaffins, glycerol esters and alkaline earth metal soaps, and also fatty ketone, and also lubricants or combinations of these, as listed in EP 0 259 783. Calcium stearate is preferred.

Plasticizers

Examples of organic plasticizers are those from the following groups:

A) Phthalates: such as preferably di-2-ethylhexyl, diisononyl and diisodecyl phthalates, also known by the common abbreviations DOP (dioctyl phthalate, di-2-ethylhexylphthalate), DINP (diisononyl phthalate), DIDP (diisodecyl phthalate).

B) Esters of aliphatic dicarboxylic acids, in particular esters of adipic, azeleic or sebacic acid: such as preferably di-2-ethylhexyl adipate and diisooctyl adipate.

C) Trimellitic esters, such as tri-2-ethylhexyl trimellitate, triisodecyl trimellitate (mixture), triisodecyl trimellitate, triisooctyl trimellitate (mixture), and also tri-$C_6$-$C_8$-alkyl, tri-$C_6$-$C_{10}$-alkyl, tri-$C_7$-$C_9$-alkyl and tri-$C_9$-$C_{11}$-alkyltrimellitate. Common abbreviations are TOTM (trioctyl trimellitate, tri-2-ethylhexyl trimellitate), TIDTM (triisodecyl trimellitate) and TITDTM (triisotridecyl trimellitate).

D) Epoxy plasticizers: these are primarily epoxidized unsaturated fatty acids, e.g. epoxidized soybean oil.

E) Polymeric plasticizers: the commonest starting materials for preparing polyester plasticizers are: dicarboxylic acids, such as adipic, phthalic, azelaic or sebacic acid; diols, such as 1,2-propanediol, 1,3-butanediol, 1,4-butanediol, 1,6-hexanediol, neopentyl glycol and diethyl glycol.

F) Phosphoric esters: a definition of these esters is given in the abovementioned "Taschenbuch der Kunststoffadditive" ["Plastics Additives Handbook"], Chapter 5.9.5, pp. 408–412. Examples of these phosphoric esters are tributyl phosphate, tri-2-ethylbutyl phosphate, tri-2-ethylhexyl phosphate, trichloroethyl phosphate, 2-ethylhexyl diphenyl phosphate, cresyl diphenyl phosphate, triphenyl phosphate, tricresyl phosphate and trixylenyl phosphate. Preference is given to tri-2-ethylhexyl phosphate, and also Reofos® 50 and 95 (Ciba Spezialitatenchemie).

G) Chlorinated hydrocarbons (paraffins)
H) Hydrocarbons
I) Monoesters, e.g. butyl oleate, phenoxyethyl oleate, tetrahydrofurfuryl oleate and alkylsulfonates.
J) Glycol esters, e.g. diglycol benzoate.

A definition of these plasticizers and examples for the same are given in "Kunststoffadditive" ["Plastics Additives", R. Gachter/H. Muller, Carl Hanser Verlag, 3. Ed., 1989, Chapter 5.9.6, pp. 412–415, and in "PVC Technology", W. V. Titow,4th Ed., Elsevier Publ., 1984, pp. 165–170. It is also possible to use mixtures of different plasticizers.

The plasticizers may be used in amounts of, for example, 5 to 20 parts by weight, expediently 10 to 20 parts by weight, based on 100 parts by weight of PVC. Rigid or semirigid PVC comprises preferably up to 10%, particularly preferably up to 5%, of plasticizer, or no plasticizer.

Pigments

Suitable substances are known to the skilled worker. Examples of inorganic pigments are $TiO_2$, pigments based on zirconium oxide, $BaSO_4$, zinc oxide (zinc white) and lithopones (zinc sulfide/barium sulfate), carbon black, carbon black-titanium dioxide mixtures, iron oxide pigments, $Sb_2O_3$, $(Ti,Ba,Sb)O_2$, $Cr_2O_3$, spinels, such as cobalt blue and cobalt green, Cd(S,Se), ultramarine blue. Examples of organic pigments are azo pigments, phthalocyanine pigments, quinacridone pigments, perylene pigments, diketopyrrolopyrrole pigments and anthraquinone pigments. $TiO_2$ in micronized form is also preferred. A definition and further descriptions are found in the "Handbook of PVC Formulating", E. J. Wickson, John Wiley & Sons, New York, 1993.

Phosphites (triesters of phosphorous acid)

Preferred organic phosphates are distearyl pentaerythritol diphosphite, trisnonylphenyl phosphite and phenyl didecyl phosphite. Other compounds which may be mentioned are diesters of phosphorous acid (with abovementioned radicals), and also monoesters of phosphorous acid (with abovementioned radicals), if desired also in the form of a salt of an alkali metal, of an alkaline earth metal, of zinc or of aluminum. These esters of phosphorous acid may also have been applied to an alumino salt compound; in this connection see also DE-A-4031818.

The organic phosphites may be used in amounts of, for example, 0.01 to 10 parts by weight, expediently 0.05 to 5 parts by weight and in particular 0.1 to 3 parts by weight, based on 100 parts by weight of PVC.

Epoxidized Fatty Acid Esters and Other Epoxycompounds

The novel stabilizer combination may additionally and preferably comprise at least one epoxidized fatty acid ester. Possible compounds here are especially esters of fatty acids from natural sources (fatty acid glycerides), such as soy oil or rapeseed oil. However, it is also possible to use synthetic products, such as epoxidized butyl oleate. Use may also be made of epoxidized polybutadiene and polyisoprene, if desired also in a partially hydroxylated form, or of glycidyl acrylate and glycidyl methacrylate as homo- or copolymer.

These epoxy compounds may also have been applied to an alumino salt compound; in this connection see also DE-A-4 031 818.

Antioxidants

Alkylated monophenols, e.g. 2,6-di-tert-butyl-4-methylphenol, alkylthiomethylphenols, e.g. 2,4-dioctylthiomethyl-6-tert-butylphenol, alkylated hydroquinones, e.g. 2,6-di-tert-butyl-4-methoxyphenol, hydroxylated thiodiphenyl ethers, e.g. 2,2'-thiobis(6-tert-butyl-4-methylphenol), alkylidene bisphenols, e.g. 2,2'-methylenebis(6-tert-butyl-4-methylphenol), benzyl compounds, e.g. 3,5,3',5'-tetratert-butyl-4,4'-dihydroxydibenzyl ether, hydroxybenzylated malonates, e.g. dioctadecyl-2,2-bis(3,5-di-tert-butyl-2 hydroxybenzyl) malonate, hydroxybenzyl aromatics, e.g. 1,3,5-tris(3,5-di-tert-butyl-4-hydroxybenzyl)-2,4,6-trimethylbenzene, triazine compounds, e.g. 2,4-bisoctylmercapto-6-(3,5-di-tert-butyl-4-hydroxyanilino)-1,3,5 triazine, phosphonates and phosphonites, e.g. dimethyl 2,5-di-tert-butyl-4 hydroxybenzylphosphonate, acylaminophenols, e.g. 4-hydroxylauranilide, esters of beta-(3,5-ditert-butyl-4-hydroxyphenyl)propionic acid, beta-(5-tert-butyl-4-hydroxy-3-methyl phenyl)propionic acid, beta-(3,5-dicyclohexyl-4 hydroxyphenyl)propionic acid, esters of 3,5-divert-butyl-4 hydroxyphenylacetic acid with mono- or polyhydric alcohols, amides of beta-(3,5-ditert-butyl-4-hydroxyphenyl)propionic acid, such as, for example, N,N'-bis(3,5-ditert-butyl-4-hydroxyphenylpropionyl) hexamethylenediamine, vitamin E (tocopherol) and derivatives.

The antioxidants may be used in amounts of, for example, 0.01 to 10 parts by weight, expediently 0.1 to 10 parts by weight and in particular 0.1 to 5 parts by weight, based on 100 parts by weight of PVC.

UV Absorbers and Light Stabilizers

Examples of these are: 2-(2'-hydroxyphenyl) benztriazoles, such as 2-(2' hydroxy-5'-methylphenyl) benzotriazole, 2-hydroxybenzophenones, esters of unsubstituted or substituted benzoic acids, such as 4-tert-butylphenyl salicylate, phenyl salicylate, acrylates, nickel compounds, oxalamides, such as 4,4'-dioctyloxyoxanilide, 2,2'-dioctyloxy-5,5'-ditert-butyloxanilide, 2-(2-hydroxyphenyl)-1,3,5-triazines, such as 2,4,6-tris(2-hydroxy-4 octyloxyphenyl)-1,3,5-triazine, 2-(2-hydroxy-4-octyloxyphenyl)-4,6-bis(2,4 dimethylphenyl)-1,3,5-triazine, sterically hindered amines, such as bis(2,2,6,6-tetramethylpiperidin-4-yl) sebacate, bis(2,2,6,6-tetramethyl-piperidin-4-yl) succinate.

Blowing Agents

Examples of blowing agents are organic azo compounds and organic hydrazo compounds, tetrazoles, oxazines, isatoic anhydride, and also soda and sodium bicarbonate. Preference is given to azodicarbonamide and sodium bicarbonate and also mixtures of these.

Definitions for and examples of impact modifiers and processing aids, gelling agents, antistats, biocides, metal deactivators, optical brighteners, flame retardants, antifogging agents and compatibilizers are given in "Kunststoffadditive" ["Plastics Additives"], R. Gachter/H. Muller, Carl Hanser Verlag, 3rd. Ed., 1989, and in "Handbook of Polyvinyl Chloride Formulating" E. J. Wilson, J. Wiley & Sons, 1993, and also in "Plastics Additives" G. Pritchard, Chapman & Hall, London, 1st Ed.,1998.

Impact modifiers are also described in detail in "Impact Modifiers for PVC", J. T. Lutz/D. L. Dunkelberger, John Wiley & Sons, 1992.

Examples of the chlorine-containing polymers to be stabilized are: polymers of vinyl chloride, of vinylidene chloride, vinyl resins whose structure contains vinyl chloride units, such as copolymers of vinyl chloride and vinyl esters of aliphatic acids, in particular vinyl acetate, copolymers of vinyl chloride with esters of acrylic or methacrylic acid and with acrylonitrile, copolymers of vinyl chloride with diene compounds and with unsaturated dicarboxylic acids or anhydrides of these, such as copolymers of vinyl chloride with diethyl maleate, diethyl fumarate or maleic anhydride, postchlorinated polymers and copolymers of vinyl chloride, copolymers of vinyl chloride and vinylidene chloride with unsaturated aldehydes, ketone and others, such as acrolein, crotonaldehyde, vinyl methyl ketone, vinyl methyl ether, vinyl isobutyl ether and the like; polymers of vinylidene chloride and copolymers of the same with vinyl chloride and with other polymerizable compounds; polymers of vinyl chloroacetate and of dichlorodivinyl ether; chlorinated polymers of vinyl acetate, chlorinated polymeric esters of acrylic acid and of alpha-substituted acrylic acid; polymers of chlorinated styrenes, such as dichlorostyrene; chlorinated rubbers; chlorinated polymers of ethylene; polymers and postchlorinated polymers of chlorobutadiene and copolymers of these with vinyl chloride, chlorinated natural or synthetic rubbers, and also mixtures of the polymers mentioned with themselves or with other polymerizable compounds. For the purposes of this invention, PVC includes copolymers with polymerizable compounds, such as acrylonitrile, vinyl acetate or ABS, where these may be suspension polymers, bulk polymers or else emulsion homopolymers or emulsion copolymers which could not be adequately stabilized using the stabilizers used hitherto. Preference is given to a PVC homopolymer, also in combination with polyacrylates. This particularly applies to products produced by the Luvitherm process.

Other possible polymers are graft polymers of PVC with EVA, ABS or MBS. Other preferred substrates are mixtures of the abovementioned homo- and copolymers, in particular vinyl chloride homopolymers, with other thermoplastic or/and elastomeric polymers, in particular blends with ABS, MBS, NBR, SAN, EVA, CPE, MBAS, PMA, PMMA, EPDM or with polylactones, in particular from the group consisting of ABS, NBR, NAR, SAN and EVA. The abbreviations used for the copolymers are familiar to the skilled worker and have the following meanings: ABS: acrylonitrile butadiene-styrene; SAN: styrene-acrylonitrile; NBR: acrylonitrile-butadiene; NAR: acrylonitrile-acrylate; EVA: ethylene-vinyl acetate. Other possible polymers are in particular styrene-acrylonitrile copolymers based on acrylate (ASA). A preferred component in this context is a polymer composition which comprises, as components (i) and (ii), a mixture of 25–75% by weight of PVC and 75–25% by weight of the copolymers mentioned. Components of particular importance are compositions made from (i) 100 parts by weight of PVC and (ii) 0–300 parts by weight of ABS and/or SAN-modified ABS and 0–80 parts by weight of the copolymers NBR, NAR and/or EVA, but in particular EVA.

For the purposes of the present invention it is also possible to stabilize in particular recycled materials of the chlorine-containing polymers, specifically the polymers described in more detail above, which have been degraded by processing, use or storage. Recycled material from PVC is particularly preferred.

These compounds which may be used concomitantly according to the invention, and also the chlorine-containing polymers, are well known to the skilled worker and are described in detail in "KunstoffadditiveII" ["Plastics Additives"], R. Gachter/H. Muller, Carl Hanser Verlag, 3rd. Ed., 1989; in DE 197 41 778 and in EP-A 99 105 418.0 of 17.03.1999, which are incorporated herein by way of reference.

The stabilization according to the invention is particularly advantageous for rigid PVC formulations for transparent and non-transparent applications, as are common in pipes, profiles and sheets. For transparent applications, use is preferably made of compounds of the formula (I) or (II) which have a melting point below about 190° C. The stabilization is also useful for semirigid and flexible formulations, and also in plastisols. The stabilization requires no heavy metal compounds (Sn stabilizers, Pb stabilizers, Cd stabilizers, Zn stabilizers).

The PVC stabilized according to the invention, which is also provided by the invention, may be prepared in a manner known per se, by using equipment known per se, such as the abovementioned processing apparatus, to mix the novel stabilizer combination and, if desired, other additives, with the PVC. The stabilizers here may be added individually or in a mixture, or else in the form of so-called masterbatches.

The PVC stabilized as in the present invention may be brought into the desired shape in a known manner. Examples of processes of this type are grinding, calendering, extruding, injection molding and spinning, and also extrusion blowmolding. The stabilized PVC may also be processed to give foams.

A PVC stabilized according to the invention is, for example, particularly suitable for hollow articles (bottles), packaging films (thermoformed films), blown films, pipes, foams, heavy profiles (window frames), thin-wall profiles, construction profiles, sidings, fittings, office sheeting and apparatus housings (computers, household devices). Preference is given to rigid PVC foam moldings and PVC pipes, for example for drinking water or waste water, pressure pipes, gas pipes, cable-duct pipes and cable protection pipes, pipes for industrial pipelines, drainpipes, outflow pipes, gutter pipes and drainage pipes. For more detail in this connection see "Kunststoffhandbuch PVC" ["Plastics Handbook PVC"], Vol. 2/2, 20 W. Becker/H. Braun, 2nd. Ed., 1985, Carl HanserVerlag, pp. 1236–1277.

4-Aminouracils are prepared by known methods.

Compounds 1 to 22 prepared are given in Table 1.

As in the remainder of the text, parts and percentages given are based on weight, unless otherwise stated.

SYNTHESIS EXAMPLE 1

A solution of 13.3 g (0.18 mol) of glycidol/10 ml of n-propanol was added dropwise with stirring at 90° C., within 25 minutes, to a mixture of 21.2 g (0.15 mol) of 4-amino-2-methoxy-2,6-pyrimidinedione, 90 ml of water and 0.3 g of sodium hydroxide. Once the addition had ended, stirring of the mixture continued for 60 minutes at 90° C. before it was cooled to 20° C. The unreacted starting material (4.1 g) was filtered off, the aqueous solution concentrated on a rotary evaporator to give a residue and the 28.2 g of residue recrystallized from 200 ml of n-propanol.

Yield: 11.4 g=41.6% of theory, beige crystals of melting point 183–184° C.

The Examples 2 and 3 listed in Table 1 were synthesized under conditions identical to those described in Example 1.

SYNTHESIS EXAMPLE 4

14.1 g (0.1 mol) of 4-amino-3-methyl-2,6-pyrimidinedione, 8.9 g (0.12 mol) of glycidol, 100 ml of water and 0.3 g of sodium hydroxide were heated at reflux for 3 h, with stirring, at 95° C. The reaction mixture was then cooled and adjusted to pH 5 using glacial acetic acid, and a slight cloudiness was filtered off and the solution concentrated on a rotary evaporator to give a residue. The 25.7 g of resin-like residue were recrystallized from 100 ml of n-propanol.

Yield: 12.8 g=59.5% of theory, white crystals of melting point 198–201° C.

The Examples 5 and 6 listed in Table 2 were synthesized under conditions identical to those described in Example 4.

SYNTHESIS EXAMPLE 7

A mixture of 28.2 g (0.2 mol) of 4-amino-3-methyl-2,6-pyrimidinedione, 90 ml of water, 10 ml of n-propanol, 0.3 g of sodium hydroxide and 34.9 g (0.3 mol) of 1,2-epoxypropyl isopropyl ether was heated at reflux for 3.5 hours, with stirring. After cooling to 10° C. the unreacted starting material was filtered off with suction and the mother liquor concentrated on a rotary evaporator to give a residue. The 55.7 g of residue were pasted with 100 ml of methyl isobutyl ketone, and the white crystals isolated and dried.

Yield: 28.9 g=56.2% of theory melting point 175–175° C. from n-propanol

Examples 8, 9, 13 and 16 listed in Table 2 were prepared using the synthesis conditions from Example 7.

SYNTHESIS EXAMPLE 10

21.7 g (0.1 mol) of 4-amino-3-benzyl-2,6-pyrimidinedione, 17.5 g (0.15 mol) of 1,2-epoxypropyl isopropyl ether, 90 ml of water, 10 ml of n-propanol and 0.4 g of sodium hydroxide were stirred at reflux for 2 hours. The reaction mixture was then cooled to 6° C., and the crystals filtered off with suction, washed with water and dried.

Yield: 26.0 g=78.1 % of theory, yellow crystals melting point: 184–186° C. (from n-propanol melting point 194–195° C.)

Examples 14, 15, 17 and 18 listed in Table 2 were prepared using the synthesis conditions from Example 7.

SYNTHESIS EXAMPLE 11

14.1 g (0.1 mol) of 4-amino-3-methyl-2,6-pyrimidinedione, 34.2 g (0.15 mol) of glycidyl neodecanoate, 30 ml of n-propanol, 70 ml of water, 2 ml of triethylamine and 2 g of tetrabutylammonium bromide were heated at reflux for 5 hours, with stirring. After cooling, the two phase reaction mixture was mixed with 100 ml of dichloromethane, and the unreacted starting material (6.7 g) was filtered off with suction, and the organic phase removed and concentrated to a residue. The 40.7 g of residue were then stirred for 30 minutes with 1200 ml of diethyl ether and the white precipitate was filtered off with suction, washed with diethyl ether and dried.

Yield: 1.3 g=30.6% of theory, white crystallized powder melting point 175–179° C. (from methyl isobutyl ketone melting point 184–185° C.)

SYNTHESIS EXAMPLE 12

A mixture of 14.1 g (0.1 mol) of 4-amino-3-methyl-2,6-pyrimidinedione, 27.9 g (0.15 mol) of 2-ethylhexyl glycidyl ether, 30 ml of n-propanol, 70 ml of water and 0.4 g of sodium hydroxide was stirred at reflux for 2 hours.

The reaction mixture was then cooled and the unreacted starting material removed by filtration (7.5 g), and the mother liquor concentrated to give a residue. The 34.5g of residue were then stirred with 50 ml of acetone/50 ml of diethyl ether and a white precipitate was isolated, washed with diethyl ether and dried.

Yield: 7.4 g=22.6% of theory, white crystals melting point 159–160° C.

SYNTHESIS EXAMPLE 19

423.3 g (3.0 mol) of 4-amino-3-methyl-2,6-pyrimidinedione, 500 g of water and 8 g of sodium hydroxide were heated in a 1.5l pressure vessel to 80° C. and reacted, with stirring, for 60minutes with 198 g (4.5 mol) of ethylene oxide at a pressure of 2–4 bar.

Stirring of the mixture was continued for 60 minutes at 85–90° C., and it was then cooled, and the white precipitate was filtered off with suction, washed with water and dried to constant weight.

Yield: 467.1 g=84.1 % of theory white crystals, melting point: 280–82° C.

Compounds 1 to 3 prepared are given in Table 1 and compounds 4 to 19 are given in Table 2.

As in the remainder of the text, parts and percentages given are based on weight, unless otherwise stated.

SYNTHESIS EXAMPLE 20

211,7 g (1.5 mol) of 4-amino-3-methyl-2,6-pyrimidinedione, 250 g of water and 6 g of sodium hydroxide were charged to a reaction vessel of 1.0l capacity, and 228.5 g (2.0 mol) of allyl glycidyl ether were added dropwise, with stirring, over a period of 50 minutes at 40° C.

Stirring of the reaction mixture continued at 40° C. for 5.75 hours, and it was then cooled to about 5° C. and the crystalline precipitate filtered off with suction. The filter cake was then washed with 2×75 ml of acetone and dried to constant weight.

Yield: 321.4 g=84.0% of theory, white crystals of melting point 150–152° C.

$^1$H-NMR shows the product to comprise 0.5 mol% of 4-amino-3-methyl-2,6 pyrimidinedione.

SYNTHESIS EXAMPLE 21

12.7g (0.1 mol) of 4-amino-2,6-dihydroxypyrimidine, 100 ml of water, 24.6 g of allyl glycidyl ether and 0.6 g of sodium hydroxide were stirred at room temperature for 120 hours. The clear yellow solution was then neutralized with 1.0 g of glacial acetic acid and concentrated on a rotary evaporator to give a residue. The residue was then dissolved in 100 ml of acetone, a cloudiness was filtered off, and the filtrate was added dropwise, with stirring, to 500 ml of ethyl acetate. A precipitate formed, which was isolated by decanting the supernatant solution and pasted with 100 ml of acetone. The undissolved fractions were filtered off and the filtrate was again concentrated to give a residue.

Residue: 28.7 g=81 % of theory, yellow viscous liquid, $N^D_{30}$: 1.5225

$^1$H-NMR shows the product to comprise 93.2% by weight of bis-2 hydroxypropyl allyl ether product and 6.8% of monosubstituted product.

SYNTHESIS EXAMPLE 22

A mixture of 25.4 g (0.2 mol) of 4 amino-2,6-dihydroxypyrimidine, 30.3 g (0.42 mol) of butene 1,2-oxide, 100 ml of water and 1.2 g of sodium hydroxide was stirred for 12 days at about 20° C. The clear solution was then neutralized with 2.0 g of glacial acetic acid, concentrated on a rotary evaporator to give a residue and dissolved with 250 ml of acetone, and a cloudiness was filtered off and the filtrate concentrated to 150 g. This solution was then stirred into 600 ml of ethyl acetate.

A highly viscous phase sedimented out. The upper phase was decanted off and concentrated to give a residue.

Residue 1 comprised 37.3 g of yellow resin.

The highly viscous sediment was dissolved in 100 ml of methanol and likewise concentrated to give a residue.

Residue 2 comprised 15.8 g of yellow resin.

$^1$H-NMR shows that residue 1 comprised 68.0% by weight of bis-2 hydroxybutylaminouracil and 32% by weight of monosubstituted 2-hydroxybutylaminouracil.

$^1$H-NMR shows that residue 2 comprised 90.5% by weight of bis-2-hydroxybutylaminouracil and 9.5% by weight of monosubstituted uracil.

SYNTHESIS EXAMPLE 23

48 g (0.38 mol) of 4-amino-2,6-dihydroxypyrimidine, 250 g of water and 2.0 g of sodium hydroxide were charged to a pressure vessel, and 44 g (1.0 mol) of ethylene oxide were added dropwise at 60° C. within a period of 10 minutes, with stirring. Stirring of the mixture continued for 30 minutes at 100° C. and at a pressure of 3 bar, and it was then cooled, and the clear, pale yellow solution concentrated to give a residue.

The 99.6 g of residue were washed with 2×200 ml of acetone and then recrystallized from 200 mol of n-propanol.

Yield: 33.8 g=41.3% of theory, white crystals of melting point 170–171° C. after recrystallization from n-propanol/water, the melting point was 183–185° C.

TABLE 1

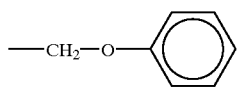

| Example | R² | R¹ | Solv. | M.P. [° C.] | Yd. [%] | Rem. |
|---------|-----|-----|-------|-------------|---------|------|
| 1 | —CH₂—OH | —CH₃ | H₂O/ⁿPrOH | 195–196 | 41.5% | from ⁿPrOH |
| 2 | —CH₂—O—CH(CH₃)₂ | —CH₃ | H₂O/ⁿPrOH | 125–127 | 49.6% | from ⁿPrOH |
| 3 | —CH₂—O—C₆H₅ | —CH₃ | H₂O/ⁿPrOH | 183–186 | 53.2% | from ⁿPrOH |

LM = Solv.

TABLE 2

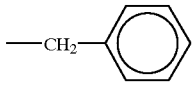

| Example | R² | R³ | X | Solv. | M.P. [° C.] | Yd. [%] | Rem. |
|---------|-----|-----|---|-------|-------------|---------|------|
| 4 | —CH₂—OH | —CH₃ | O | H₂O | 198–201 | 60 | from ⁿPrOH |
| 5 | —CH₂—OH | —CH₂—CH₂—CH₃ | O | H₂O | 143–146 | 44 | from ⁿPrOH/acetone |
| 6 | —CH₂—OH | —CH₂—C₆H₅ | O | H₂O ⁿPrOH | 184–186 | 59 | from ⁿPrOH still comprises about 1 mol of ⁿPROH |
| 7 | —CH₂—O—CH(CH₃)₂ | —CH₃ | O | H₂O ⁿProH | 175–176 (not clear) | 60 | from ⁿPrOH |

TABLE 2-continued

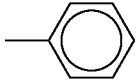

| Example | R² | R³ | X | Solv. | M.P. [° C.] | Yd. [%] | Rem. |
|---|---|---|---|---|---|---|---|
| 8 | —CH₂—O—CH(CH₃)₂ | —C₆H₄—CH₃ (tolyl) | O | H₂O/ⁿPrOH | 138–141 | 35 | from methy tert-butyl ether |
| 9 | —CH₂—O—C(CH₃)₃ | —CH₃ | O | H₂O/ⁿPrOH | 180 | 67 | from ⁿPrOH |
| 10 | —CH₂—O—CH(CH₃)₂ | —CH₂—C₆H₅ | O | H₂O/ⁿPrOH | 194–195 | 78 | from ⁿPrOH |
| 11 | —CH₂—O—CO-neo-C₉H₁₉ | —CH₃ | O | H₂O/ⁿPrOH | 184–185 | 31 | from MIBK |
| 12 | —CH₂—O—CH₂—CH(CH₂—CH₃)—ⁿC₄H₉ | —CH₃ | O | H₂O/ⁿPrOH | 161–162 | 23 | |
| 13 | —CH₃ | —CH₃ | O | H₂O/ⁿPrOH | 216–218 | 78 | from H₂O/ⁿPrOH |
| 14 | —CH₃ | —CH₂—C₆H₅ | O | H₂O/ⁿPrOH | 187–188 | 70 | from H₂O/ⁿPrOH |
| 15 | —ⁿC₄H₉ | —CH₃ | O | H₂O/ⁿPrOH | 199–200 | 28 | from ⁿPrOH |
| 16 | —CH₂—CH₃ | —CH₃ | O | H₂O/ⁿPrOH | 187 | 78 | from H₂O/ⁿPrOH |
| 17 | —CH₂—CH₃ | —CH₂—C₆H₅ | O | H₂O/ⁿPrOH | 160–163 | 86 | from ⁿPrOH |
| 18 | —CH₂—O—CH(CH₃)₂ | —CH₂—C₆H₅ | S | H₂O/ⁿPrOH | 191–192 | 35 | from ⁿPrOH |
| 19 | H | —CH₃ | O | H₂O | 284–85 | 84 | from ⁿPrOH/H₂O |
| 20 | —CH₂—O—CH₂—CH=CH₂ | —CH₃ | O | H₂O | 150–152 | 84 | — |

LM = Solv.

TABLE 3

$$\underset{\underset{H}{\overset{H}{N}}\phantom{wide}\underset{NH_2}{\overset{O}{\underset{N}{\|}}}}{} + 2\ \underset{CH_2-CH-R^2}{\overset{O}{\triangle}} \xrightarrow[\text{Base (e.g. NaOH)}]{LM} \underset{\underset{CH_2-CH-R^2}{\underset{OH}{|}}}{\overset{R^2-HC-H_2C}{\underset{N}{\|}}\underset{NH_2}{\overset{O}{\underset{N}{\|}}}}$$

| Example | R² | X | Solv. | M.P. [° C.] | Yd. [%] | Rem. |
|---|---|---|---|---|---|---|
| 21 | —CH₂—O—CH₂—CH=CH₂ | O | H₂O | — | 81 | $n_{D30}$: 1.5225 |
| 22 | —CH₂—CH₃ | O | H₂O | — | — | yellow resin |
| 23 | H | O | H₂O | 170–171 | 41 | from ⁿPrOH/H₂O |

LM = Solv.

EXAMPLE I

Statistical heat test

A dry mixture composed of 100.0 part Evipol[1])SH5730=PVC K value 57

5.0 parts Paraloid[2])BTA III N2=MBS (=methyl methacrylate-butadiene-styrene) modifier 0.5 part Paraloid[2])K 120 N=acrylate processing aid 0.5 part Paraloid[2])K 175=acrylate processing aid 0.3 part Wachs E—ester wax (montan wax) (ex BASF)

0.1 part Loxiol® G 16=partial fatty acid ester of glycerol (ex Henkel)

3.0 parts ESO—epoxidized soybean oil and one of the stabilizers given in Table 4 was milled on mixing rolls at 180° C. for 5 minutes. Test strips of sheet thickness 0.3 mm were taken from the milled sheet formed. The specimens of sheets were exposed to heat in an oven (Mathis-Thermo-Takter) at 190° C. At intervals of 3 minutes the Yellowness Index (YI) was determined to ASTM D-1925–70. The results are given in Table 5 below. Low YI values mean good stabilization.

[1]) Trademark of EVC
[2]) Trademark of Rohm & Haas

EXAMPLE II

Pressed sheets

A dry mixture composed of 100.0 part Evipol[1])SH5730=PVC K value 57

5.0 parts Paraloid[2])BTA III N2=MBS (=methyl methacrylate-butadiene-styrene) modifier 0.5 part Paraloid[2])K 120 N=acrylate processing aid 0.5 part Paraloid[2])K 175=acrylate processing aid 0.3 part Wachs E—ester wax (montan wax) (ex BASF)

0.1 part Loxiol® G 16=partial fatty acid ester of glycerol (ex Henkel)

3.0 parts ESO—epoxidized soybean oil and one of the stabilizers given in Table 5 was milled on mixing rolls at 180° C. for 5 minutes. The resultant milled sheets were press-molded at 180° C. for 1.5 minutes and at a pressure of 200 bar, to give segmented pressed sheets of thickness 1 mm. The Yellowness Index at ASTM D-1925-70 of these pressed sheets and their transparency to ASTM D-2805-80 or, respectively, ASTM D-589-65 were determined. The results are given in Table. 4. Low YI values mean good stabilization and high transparency values mean good transparency of the test specimens produced.

[1]) Trademark of EVC
[2]) Trademark of Rohm & Haas

TABLE 4

| Minutes | Without stabilizer | Stabilizer 1 1.0 part | Stabilizer 4 1.0 part | Stabilizer 5 1.0 part | Stabilizer 7 1.0 part | Stabilizer 10 1.0 part | Stabilizer 15 1.0 part |
|---|---|---|---|---|---|---|---|
| 0 | 68.10 | 18.46 | 10.82 | 6.99 | 6.35 | 7.57 | 7.17 |
| 3 | 75.63 | 26.47 | 13.37 | 9.63 | 7.28 | 8.94 | 7.89 |
| 6 | 99.65 | 34.26 | 17.15 | 12.31 | 8.64 | 10.93 | 8.97 |
| 9 | 130.67 | 42.97 | 23.47 | 16.06 | 11.78 | 14.71 | 11.68 |
| 12 | | 57.90 | 31.26 | 22.80 | 15.35 | 19.85 | 15.29 |
| 15 | | 72.50 | 40.88 | 29.16 | 19.91 | 26.10 | 20.81 |
| 18 | | 92.40 | 49.99 | 38.14 | 26.03 | 34.46 | 27.13 |
| 21 | | 113.38 | 61.17 | 48.49 | 32.42 | 45.56 | 35.59 |
| 24 | | | 71.59 | 60.27 | 44.46 | 60.81 | 47.93 |
| 27 | | | 87.03 | 74.30 | 63.65 | 76.53 | 68.02 |
| 30 | | | 104.81 | 98.01 | 145.02 | 105.32 | 209.84 |

Key
Stabilizer 1 = Stabilizer of Synthesis Example 1
Stabilizer 4 = Stabilizer of Synthesis Example 4
Stabilizer 5 = Stabilizer of Synthesis Example 5
Stabilizer 7 = Stabilizer of Synthesis Example 7
Stabilizer 10 = Stabilizer of Synthesis Example 10
Stabilizer 15 = Stabilizer of Synthesis Example 15

TABLE 5

| Results | Without stabilizer | Stabilizer 4 | Stabilizer 5 | Stabilizer 7 | Stabilizer 10 | 0 Stabilizer 15 | Stabilizer 16 |
|---|---|---|---|---|---|---|---|
| YI | 190.1 | 34.7 | 19.9 | 14.5 | 16.0 | 11.7 | 9.2 |
| Transparency (%) | 41.4 | 86.3 | 92.8 | 91.4 | 95.4 | 96.3 | 95.2 |

Key
Stabilizer 4 = Stabilizer of Synthesis Example 4
Stabilizer 5 = Stabilizer of Synthesis Example 5
Stabilizer 7 = Stabilizer of Synthesis Example 7
Stabilizer 10 = Stabilizer of Synthesis Example 10
Stabilizer 15 = Stabilizer of Synthesis Example 15
Stabilizer 16 ≦ Stabilizer of Synthesis Example 16

What is claimed is:

1. A compound of the general formula

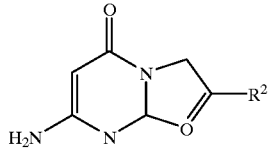

where $R^2$ is hydrogen, $C_1$–$C_{14}$ alkyl, $C_2$–$C_4$ alkenyl, $C_4$–$C_8$ cycloalkyl, $C_4$–$C_8$ cycloalkyl substituted with $R^4$, $C_6$–$C_{10}$ aryl, $C_6$–$C_{10}$ aryl substituted with $R^4$, $C_7$–$C_{10}$ alkaryl, $C_7$–$C_{10}$ alkaryl substituted with $R^4$, $C_7$–$C_{10}$ aralkyl, $C_7$–$C_{10}$ aralkyl substituted with $R^4$, —$CH_3X$ or —$CH_3X$ substituted with $R^4$;

X is oxygen or sulfur; and $R^4$ is $C_1$–$C_{10}$ alkyl, $C_2$–$C_4$, alkenyl, $C_4$–$C_8$ cycloalkyl, $C_1$–$C_{10}$ alkyl containing an oxirane ring, $C_2$–$C_4$ alkenyl containing an oxirane ring, $C_4$–$C_8$ cycloalkyl containing an oxirane ring, $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups, $C_4$–$C_8$ cycloalkyl substituted with up to 3 $C_1$–$C_4$ alkyl groups, benzoyl or $C_2$–$C_{18}$ acyl.

2. A compound in accordance with claim 1 wherein $R_2$ is hydrogen, methyl, ethyl, allyl, phenyl, —$CH_3X$ or —$CH_3X$ substituted with n-propyl, isopropyl, 2-ethylhexyl, n-butyl, isobutyl, sec-butyl, tert-butyl, allyl, methallyl, phenyl or cresyl.

3. A compound in accordance with claim 2 wherein $R^2$ is ethyl, —$CH_3X$ or —$CH_3X$ substituted with isopropyl, n-butyl or allyl; and X is oxygen.

4. A compound in accordance with claim 1 wherein $R^4$ is $C_1$–$C_{10}$ alkyl containing an oxirane ring, $C_2$–$C_4$ alkenyl containing an oxirane ring or $C_4$–$C_8$ cycloalkyl containing an oxirane ring.

5. A compound in accordance with claim 1 wherein $R^4$ is $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups or $C_4$–$C_8$ cycloalkyl substituted with up to 3 $C_1$–$C_4$ alkyl groups.

6. A process for preparing a compound of the general formula

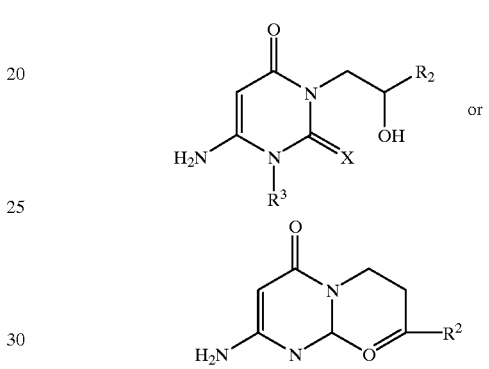

where $R^2$ is hydrogen, $C_1$–$C_{14}$ alkyl, $C_2$–$C_4$ alkenyl, $C_4$–$C_8$ cycloalkyl, $C_4$–$C_8$ cycloalkyl substituted with $R^4$, $C_6$–$C_{10}$ aryl, $C_6$–$C_{10}$ aryl substituted with $R^4$, $C_7$–$C_{10}$ alkaryl, $C_7$–$C_{10}$ alkaryl substituted with $R^4$, $C_7$–$C_{10}$ aralkyl, $C_7$–$C_{10}$ aralkyl substituted with $R^4$, —$CH_3X$ or —$CH_3X$ substituted with $R^4$;

X is oxygen or sulfur; and $R^4$ is $C_1$–$C_{10}$ alkyl, $C_2$–$C_4$ alkenyl $C_4$–$C_8$ cycloalkyl, $C_1$–$C_{10}$ alkyl containing an oxirane ring, $C_2$–$C_4$ alkenyl containing an oxirane ring, $C_4$–$C_8$ cycloalkyl containing an oxiraiie ring, $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups, $C_4$–$C_8$ cycloalkyl substituted with up to 3 $C_1$–$C_4$ alkyl groups, benzoyl or $C_2$–$C_{18}$ acyl;

$R^3$ is $R^2$, $R^4$, $C_2$–$C_6$ alkyl substituted with at least 1 to 5 hydroxyl groups, $C_2$–$C_6$ alkyl interrupted by at least 1 but not more than 4 oxygen atoms, $C_3$–$C_8$ alkenyl or —$CH_2CH(OH)R^2$ comprising reacting a compound of the general formula

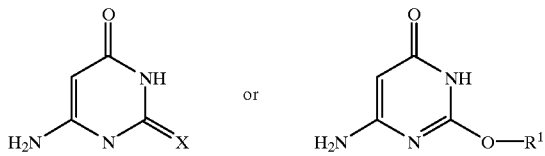

where $R^1$ is a branched or unbranched $C_1$–$C_4$ alkyl radical, with an epoxy compound having the general formula

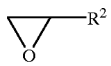

where $R^2$ has the meanings given above, in a solvent, and in the presence of a catalytically effective amount of a base, at a temperature in the range of between 20° C. and 150° C.

7. A process in accordance with claim 6 wherein $R^4$ is $C_1$–$C_{10}$ alkyl containing an oxirane ring, $C_2$–$C_4$ alkenyl containing an oxirane ring or $C_4$–$C_8$ cycloalkyl containing an oxirane ring.

8. A process in accordance with claim 6 wherein $R^4$ is $C_1$–$C_{10}$ alkyl substituted with up to 3 $C_{1-C4}$ alkyl groups, $C_2$–$C_4$ alkenyl substituted with up to 3 $C_1$–$C_4$ alkyl groups or $C_4$–$C_8$ cycloalkyl substituted with up to 3 $C_1$–$C_{-4}$ alkyl groups.

9. A process in accordance with claim 6 wherein said process occurs at elevated pressure.

10. A stabilizer comprising (A) from 0.01 to 10 parts by weight, per 100 parts by weight of a chlorine-containing polymer, of a compound having the formula

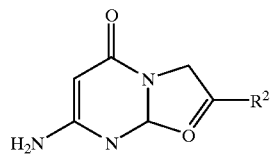

where $R^2$ is hydrogen, $C_1$–$C_{14}$ alkyl, $C_2$–$C_4$ alkenyl, $C_4$–$C_8$ cycloalkyl, $C_4$–$C_8$ cycloalkyl substituted with $R^4$, $C_6$–$C_{10}$ aryl, $C_6$–$C_{10}$ aryl substituted with $R^4$, $C_7$–$C_{10}$ alkaryl, $C_7$–($C_{10}$ alkaryl substituted with $R^4$, $C_7$–$C_{10}$ aralkyl, $C_7$–$C_{10}$ aralkyl substituted with $R^4$, —$CH_3X$ or —$CH_3X$ substituted with $R^4$, X is oxygen or sulfur; and $R^4$ is $C_1$–$C_{10}$ alkyl, $C_2$–$C_4$ alkenyl, $C_4$–$C_8$ cycloalkyl, $C_1$–$C_{10}$ alkyl containing an oxirane ring, $C_2$–$C_4$ alkenyl containing an oxirane ring, $C_4$–$C_8$ cycloalkyl containing an oxirane ring, $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups, $C_4$–$C_8$ cycloalkyl substituted with up to 3 $C_{-C4}$ alkyl groups, benzoyl or $C_2$–$C_{18}$ aryl; and (B) at least one compound selected from the group consisting of polyols, disaccharide alcohols, perchlorate compounds, glycidyl compounds, epoxy compounds, hydrotalcites, dawsonites, alkali metal aluminosilicates, alkaline earth metal aluminosilicates, metal soaps, alkali metal oxides, alkali metal hydroxides, alkali metal carboxylates, alkali metal carbonates, alkaline earth metal oxides, alkaline earth metal hydroxides, alkaline earth metal carboxylates, alkaline earth metal carbonates, phosphites, antioxidants, light stabilizers, lubricants, plasticizers, pigments and fillers.

11. A stabilizer in accordance with claim 10 wherein $R^2$ is hydrogen, methyl, ethyl, phenyl, —$CH_3X$ or —$CH_3X$ substituted with $R^4$; and $R^4$ is n-propyl, isopropyl, 2-ethylhexyl, n-butyl, isobutyl, sec-butyl, tert-butyl, allyl, methallyl, phenyl or cresyl.

12. A process of stabilizing chlorine-containing polymers comprising incorporating into a chlorine-containing polymer (A) 0.1 to 10 parts by weight, based on 100 parts by weight of said chlorine-containing polymer, at least one compound having the general formula

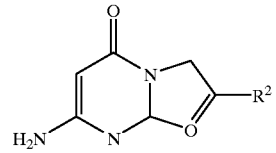

where $R^2$ is hydrogen, $C_1$–$C_4$ alkyl, $C_2$–$C_4$ alkenyl, $C_4$–$C_8$ cycloalkyl, $C_4$–$C_8$ cycloalkyl substituted with $R^4$, $C_6$–$C_{10}$ aryl, $C_6$–$C_{10}$ aryl substituted with $R^4$, $C_7$–$C_{10}$ alkaryl, $C_7$–$C_{10}$ alkaryl substituted with $R^4$, $C_7$–$C_{10}$ aralkyl, $C_7$–$C_{10}$ aralkyl substituted with $R^4$, —$CH_3X$ or —$CH_3X$ substituted with $R^4$;

X is oxygen or sulfur; and $R^4$ is $C_1$–$C_{10}$alkyl, $C_2$–$C_4$, alkenyl, $C_4$–$C_8$ cycloalkyl, $C_1$–$C_{10}$ alkyl containing an oxirane ring, $C_2$–$C_4$ alkenyl containing an oxirane ring, $C_4$–$C_8$ cycloalkyl containing an oxirane ring, $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups, $C_4$–$C_8$ cycloalkyl substituted with 1 to 3 alkyl groups, benzoyl or $C_2$–$C_{18}$ acyl; and (B) at least one compound selected from the group consisting of polyols, disaccharide alcohols, perchlorate compounds, glycidyl compounds, epoxy compounds, hydrotalcites, dawsonites, alkali metal aluminosilicates, alkaline earth metal aluminosilicates, metal soaps, alkali metal oxides, alkali metal hydroxides, alkali metal carbonates, alkali metal carboxylates, alkaline earth metal oxides, alkaline earth metal hydroxides, alkaline earth metal carbonates, alkaline earth metal carboxylates, phosphites, antioxidants, light stabilizers, lubricants, plasticizers, pigments and fillers.

13. A process as claimed in claim 12 where $R^4$ is $C_1$–$C_{10}$ alkyl containing an oxirane ring, $C_2$–$C_4$ alkenyl containing an oxirane ring or $C_4$–$C_8$ cycloalkyl containing an oxirane ring.

14. A process as claimed in claim 12 where $R^4$ is $C_1$–$C_{10}$ alkyl substituted with up to 3 $C_1$–$C_4$ alkyl groups, $C_2$–$C_4$ alkenyl substituted with Up to 3 $C_1$–$C_4$ alkyl groups or $C_4$–$C_8$ cycloalkyl substituted with 1 to 3 $C_1$–$C_4$ cycloalkyl groups.

15. A composition comprising a chlorine-containing polymer and (A) from 0.01 to 10 parts by weight, leased on 100 parts by weight of said chloride-containing polymer, of

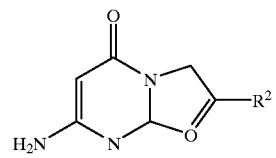

where $R^2$ is hydrogen, $C_1$–$C_{14}$ alkyl, $C_2$–$C_4$ alkenyl, $C_4$–$C_8$ cycloalkyl, $C_4$–$C_8$ cycloalkyl substituted with $R^4$, $C_6$–$C_{10}$ aryl, $C_6$–$C_{10}$ aryl substituted with $R^4$, $C_7$–$C_{10}$ alkaryl, $C_7$–$C_{10}$ alkaryl substituted with $R^4$, $C_7$–$C_{10}$ aralkyl, $C_7$–$C_{10}$ aralkyl substituted with $R^4$, —$CH_3X$ or —$CH_3X$ substituted with $R^4$;

X is oxygen or sulfur; and $R^4$ is $C_1$–$C_{10}$ alkyl, $C_2$–$C_4$ alkenyl, $C_4$–$C_8$ cyclically, any of the above three radicals containing an oxarine ring, any of the above three radicals substituted with up to 3 $C_1$–$C_3$ alkyl groups, benzoyl or $C_2$–$C_{18}$ acyl; and (B) at least one compound selected from the group consisting of polyols, disaccharide alcohols, perchlorate compounds, glycidyl compounds, epoxy compounds, hydrotalcites, dawsonites, alkali metal aluminosilicates, alkaline earth metal aluminosilicates, metal soaps, alkali metal oxides, alkali metal hydroxides, alkali metal carbonates, alkali metal carboxylates, alkaline earth metal oxides, alkaline earth metal hydroxides, alkaline earth metal carbonates, alkaline earth metal carboxylates, phosphites, antioxidants, light stabilizers, lubricants, plasticizers, pigments and fillers.

16. A composition in accordance with claim 15 where $R^4$ is $C_1$–$C_{10}$ alkyl containing an oxirane ring, $C_2$–$C_4$ alkenyl containing an oxirane ring or $C_4$–$C_8$ cycloalkyl containing an oxarine ring.

17. A composition in accordance with claim 15 where $R^4$ is $C_1$–$C_{10}$ substituted with up to 3 $C_1$–$C_{14}$ alkyl groups, $C_2$–$C_4$ alkenyl substituted with up to 3 $C_1$–$C_4$ alkyl groups or $C_4$–$C_8$ cycloalkyl substituted with up to 3 $C_1$–$C_4$ alkyl groups.

18. A process in accordance with claim 12 wherein $R^2$ is —$CH_3X$ substituted with $R^4$, hydrogen, methyl, ethyl or phenyl; and $R^4$ is n-propyl, isopropyl, 2-ethylhexyl, n-butyl, isobutyl, sec-butyl, tert-butyl, allyl, methallyl, phenyl or cresyl.

19. A stabilizer combination in accordance with claim 10 wherein $R^4$ is $C_1$–$C_{10}$ alkyl containing an oxirane ring, $C_2$–$C_4$ alkenyl containing an oxirane ring or $C_4$–$C_8$ cycloalkyl containing an oxirane ring.

20. A stabilizer combination in accordance with claim 10 wherein $R^4$ is $C_1$–$C_{10}$ alkyl substituted with up to 3 $C_1$–$C_4$ alkyl groups, $C_2$–$C_4$ alkenyl substituted with up to 3 $C_1$–$C_4$ alkyl groups or $C_4$–$C_8$ cycloalkyl substituted with up to 3 $C_1$–$C_4$ alkyl groups.

* * * * *